United States Patent
Tackmann et al.

(10) Patent No.: US 10,094,214 B2
(45) Date of Patent: Oct. 9, 2018

(54) GAS DETECTION BASED ON EVANESCENT COUPLING FROM WAVEGUIDES IN BULK SUBSTRATES TO DOWNHOLE FLUIDS

(71) Applicant: BAKER HUGHES INCORPORATED, Houston, TX (US)

(72) Inventors: Gunnar Tackmann, Lower Saxony (DE); Sebastian Jung, Isernhagen (DE); Thomas Kruspe, Wietzendorf (DE)

(73) Assignee: BAKER HUGHES, A GE COMPANY, LLC, Houston, TX (US)

( * ) Notice: Subject to any disclaimer, the term of this patent is extended or adjusted under 35 U.S.C. 154(b) by 0 days.

(21) Appl. No.: 15/091,992

(22) Filed: Apr. 6, 2016

(65) Prior Publication Data

US 2017/0292374 A1  Oct. 12, 2017

(51) Int. Cl.
 *E21B 49/08* (2006.01)
(52) U.S. Cl.
 CPC .................................. *E21B 49/08* (2013.01)
(58) Field of Classification Search
 CPC ...... E21B 49/08; E21B 49/085; E21B 49/087; G01N 21/648; G02B 6/02057;
 (Continued)

(56) References Cited

U.S. PATENT DOCUMENTS 5,525,800 A  6/1996  Sanghera et al.
6,198,861 B1  3/2001  Kellar et al.
(Continued)

FOREIGN PATENT DOCUMENTS

DE  19651644 A1  6/1997
WO  2014207089 A1  12/2014

OTHER PUBLICATIONS

Phillip H. Paul et al., "Fiber-Optice Evanescent Field Absorption Sensor," App. Phys. Lett. 51(1), pp. 12-14 (Jul. 6, 1987).
(Continued)

*Primary Examiner* — Casey Bryant
(74) *Attorney, Agent, or Firm* — Mossman, Kumar & Tyler, PC (57) ABSTRACT

Methods, systems, devices, and products for estimating a parameter of interest of a downhole fluid in a borehole intersecting an earth formation. Apparatus include evanescent wave measurement instruments, which may include a substrate configured for contact with a downhole fluid such that at least a portion of the substrate is immersed in the downhole fluid; a waveguide formed in an interior of the substrate and having a configuration geometrically configured to generate an interaction between the downhole fluid and an evanescent wave arising from electromagnetic energy propagating in a segment of the waveguide; and a detector configured to generate measurement information indicative of the downhole fluid in response to electromagnetic signals received from the waveguide responsive to the interaction. The interaction may result in absorption of at least a portion of the electromagnetic energy propagating in the waveguide. The waveguide may be written in the substrate using laser pulses.

25 Claims, 7 Drawing Sheets

(58) Field of Classification Search
CPC ........ G02B 6/02061; G02B 6/29331–6/29335;
G02B 6/3522
See application file for complete search history.

(56) References Cited

U.S. PATENT DOCUMENTS

| | | | | |
|---|---|---|---|---|
| 6,995,360 | B2* | 2/2006 | Jones | B08B 7/028 |
| | | | | 250/269.1 |
| 7,969,571 | B2* | 6/2011 | DiFoggio | E21B 47/00 |
| | | | | 250/269.1 |
| 2002/0125589 | A1* | 9/2002 | Katzir | G01N 21/552 |
| | | | | 264/1.23 |
| 2004/0094716 | A1* | 5/2004 | Evan Webber | G01N 21/1702 |
| | | | | 250/339.12 |
| 2009/0216419 | A1 | 8/2009 | Shaw | |
| 2014/0300889 | A1* | 10/2014 | DiFoggio | G01N 21/4133 |
| | | | | 356/51 |
| 2015/0144776 | A1* | 5/2015 | Jung | E21B 49/087 |
| | | | | 250/269.1 |
| 2016/0266036 | A1* | 9/2016 | Freese | G01N 21/51 |

OTHER PUBLICATIONS

D. Bunimovich et al., "Fiberoptice Evanescent Wave Infrared Spectroscopy of Gases in Liquids," Rev. Sci. Instrum. 66(4) pp. 2818-2820 (Apr. 1995).
K.M. Davis, et al., "Writing Waveguides in Glass With a Femtosecond Laser," Optics Letters, vol. 21, No. 21. pp. 1729-1731 (Nov. 1996).
Y. Raichlin et al., "Fiber-Optic Evanescent Wave Spectroscopy in the Middle Infrared," Applied Spectroscopy vol. 62, No. 2, pp. 55A-72A (2008).

* cited by examiner

GAS DETECTION BASED ON EVANESCENT COUPLING FROM WAVEGUIDES IN BULK SUBSTRATES TO DOWNHOLE FLUIDS

FIELD OF THE DISCLOSURE

This disclosure generally relates to borehole tools, and in particular to methods and apparatus for conducting downhole measurements.

BACKGROUND OF THE DISCLOSURE

Drilling wells for various purposes is well-known. Such wells may be drilled for geothermal purposes, to produce hydrocarbons (e.g., oil and gas), to produce water, and so on. Well depth may range from a few thousand feet to 25,000 feet or more. In hydrocarbon wells, downhole tools often incorporate various sensors, instruments and control devices in order to carry out any number of downhole operations. Thus, the tools may include sensors and/or electronics for formation evaluation, fluid analysis, monitoring and controlling the tool itself, and so on.

SUMMARY OF THE DISCLOSURE

In aspects, the present disclosure is related to apparatus and methods for estimating a parameter of interest of a downhole fluid in a borehole intersecting an earth formation. The apparatus may comprise an evanescent wave measurement instrument, which may include a substrate configured for contact with a downhole fluid such that at least a portion of the substrate is immersed in the downhole fluid; a waveguide formed in an interior of the substrate and having a configuration geometrically configured to generate an interaction between the downhole fluid and an evanescent wave arising from electromagnetic energy propagating in a segment of the waveguide; and a detector configured to generate measurement information indicative of the downhole fluid in response to electromagnetic signals received from the waveguide responsive to the interaction.

The interaction may result in absorption of at least a portion of the electromagnetic energy propagating in the waveguide. The interaction may results in a modification of an effective refractive index of the waveguide. The configuration may include waveguide dimensions and a waveguide path within the substrate. The waveguide path may be asymmetric with respect to the substrate. The substrate may comprise at least one flat surface. The substrate may comprise a bulk substrate. The bulk substrate may have a minimum thickness of at least 1 millimeter in a direction perpendicular to the interface. The waveguide may have a maximum thickness less than 100 µm in a direction perpendicular to a longitudinal axis of the waveguide. The ratio of the minimum thickness of the substrate to the maximum thickness of the waveguide may be at least 5 to 1, or at least 10 to 1.

Waveguide may include Bragg grating, which may be written on the interior of the waveguide. Waveguide may include Bragg grating configured to produce a reflection spectrum matching a spectral property detected by the detector, which may be written on the interior of the waveguide. Waveguide may include Bragg grating configured to produce a reflection spectrum matching a spectral property detected by the detector doubled. The waveguide may be geometrically configured via dimensions and path within the substrate to generate a second interaction between the downhole fluid and a second evanescent wave arising from electromagnetic energy propagating in a second segment of the waveguide. An additional detector may be configured to generate measurement information indicative of the second interaction. The segment may have a first length and the second segment may have a second length different than the first length. The waveguide may be formed by applying laser pulses to the substrate.

The substrate may include a plurality of waveguides formed in an interior of the substrate, each waveguide of the plurality of waveguides having a configuration geometrically configured to generate a respective interaction between the downhole fluid and a corresponding evanescent wave arising from electromagnetic energy propagating in a corresponding segment of the respective waveguide. Embodiments may include at least one detector configured to generate measurement information indicative of each respective interaction.

The waveguide of the plurality of waveguides may have a configuration including first waveguide dimensions and a first waveguide path within the substrate; and a second waveguide of the plurality of waveguides may have second waveguide dimensions and a second waveguide path within the substrate. The first waveguide dimensions may be different than the second waveguide dimensions; and the first waveguide path may be different than the second waveguide path.

The measurement instrument may measure values of the parameter of interest at a plurality of positions over the substrate and maps the values according to position. The substrate may include a plurality of waveguides formed in an interior of the substrate, with a reference waveguide of the plurality of waveguides geometrically configured via dimensions and path within the substrate to generate a respective interaction between a reference fluid and a corresponding evanescent wave arising from electromagnetic energy propagating in a corresponding segment of the reference waveguide. The measurement instrument may include at least one detector configured to generate measurement information indicative of the reference fluid in response to electromagnetic signals received from the reference waveguide; and at least one processor configured to estimate the parameter of interest using measurement information generated from the reference waveguide.

The apparatus may include a processor configured to estimate the parameter of interest using the measurement information. The parameter of interest may be a concentration of a gas in the fluid. The concentration of the gas may be used to identify an impending kick.

Apparatus embodiments may include a carrier associated with the evanescent wave measurement instrument and configured for conveyance in the borehole.

Methods may include conveying an evanescent wave measurement instrument in the borehole, where the evanescent wave measurement instrument comprises a substrate; placing the substrate into contact with a downhole fluid such that at least a portion of the substrate is immersed in the downhole fluid; using electromagnetic energy to generate an interaction between the downhole fluid and an evanescent wave arising from electromagnetic energy propagating in a segment of waveguide formed in the substrate, the evanescent wave extending into an interaction region within the downhole fluid; generating measurement information by detecting electromagnetic signals from the waveguide responsive to the interaction; and estimating a parameter of interest using the measurement information.

Embodiments may include at least one processor and a computer memory accessible to the at least one processor.

The computer memory may have disposed therein instructions that, when executed by a processor, cause the at least one processor to execute one or more methods or method components as described herein. The instructions may be disposed on a non-transitory computer-readable medium product accessible to the processor.

Examples of some features of the disclosure may be summarized rather broadly herein in order that the detailed description thereof that follows may be better understood and in order that the contributions they represent to the art may be appreciated.

BRIEF DESCRIPTION OF THE DRAWINGS

For a detailed understanding of the present disclosure, reference should be made to the following detailed description of the embodiments, taken in conjunction with the accompanying drawings, in which like elements have been given like numerals, wherein.

DETAILED DESCRIPTION

Aspects of the present disclosure relate to apparatus and methods for downhole logging with respect to formation evaluation, including measurement and interpretation of physical phenomena indicative of parameters of interest of the formation, the borehole, or the downhole fluids therein. Techniques described herein are particularly suited to measurement of values of properties of a downhole fluid through the use of instruments utilizing evanescent wave phenomena. These values may be used to evaluate and model the formation or the borehole, and for conducting further operations in the formation or the borehole.

Aspects of the present disclosure relate to modeling a volume of an earth formation. The model of the earth formation generated and maintained in aspects of the disclosure may be implemented as a representation of the earth formation stored as information. The information (e.g., data) may be stored on a non-transitory machine-readable medium, transmitted, and rendered (e.g., visually depicted) on a display.

It is known to obtain spectroscopic measurements of fluids using absorption of an evanescent field of a light wave. As used herein, the term "fluid" and "fluids" refers to one or more gasses, one or more liquids, and mixtures thereof. A "downhole fluid" as used herein includes any gas, liquid, flowable solid and other materials having a fluid property and relating to hydrocarbon recovery. A downhole fluid may be natural or man-made and may be transported downhole or may be recovered from a downhole location. Non-limiting examples of downhole fluids include drilling fluids, return fluids, formation fluids, production fluids containing one or more hydrocarbons, engineered fluids, oils and solvents used in conjunction with downhole tools, water, brine, and combinations thereof. An "engineered fluid" may be used herein to mean a human made fluid formulated for a particular purpose.

Evanescent waves may be formed when waves traveling in a medium undergo total internal reflection at its boundary because the waves strike at an angle greater than the critical angle. In one example, infrared or near-infrared light undergoes multiple internal reflections in a waveguide having a high refractive index, such as, for example, a crystal. These waves interact with a fluid, and some of the energy will be absorbed. As a result, as the light exits the waveguide, the lost energy may be analyzed and correlated with properties of the fluid. The evanescent phenomena enables spectroscopic measurements, as well as selective detection of particular fluids present on the surface of a substrate, via the spectrally selective attenuation of the evanescent field of light propagating in the waveguide. To provide the evanescent phenomena, the light inside the waveguide should propagate substantially at the substrate-to-fluid interface, thus producing a sufficiently intense evanescent field in the fluid. One technology based on this concept is referred to as Attenuated Total Reflection (ATR).

In aspects, the present disclosure relates to making downhole measurements. Downhole measurement, as used herein, may be defined as a measurement taken in a borehole intersecting an earth formation indicative of a parameter of the borehole, the formation, or a downhole fluid therein (i.e., a downhole parameter). Making the measurement is carried out using at least one waveguide. As in conventional ATR, electromagnetic energy is applied to the waveguide, resulting in an evanescent wave propagating in a portion of the waveguide. This evanescent wave interacts with the downhole fluid in an interaction region in the fluid, resulting in adsorption of some of the electromagnetic energy.

Previous examples of downhole evanescent wave measurement utilized a flexible wave guide generally covered with cladding, described in greater detail in U.S. Pat. No. 7,969,571 B2 to DiFoggio, the entirety of which is herein incorporated by reference. In desired regions for interaction, the flexible core was exposed to the fluid to be measured. While this technique has proven useful, aspects of the present disclosure offer improvement in several areas.

Aspects of the present disclosure include an evanescent wave measurement instrument (EMI) having one or more waveguides formed within a bulk substrate. That is, a portion of the substrate is converted to waveguide. The approach offers several advantages. The conversion of desired portions of the substrate to waveguide may allow for more delicate and precise fabrication of the waveguide (within the substrate) within strict tolerances, and is especially effective in positioning the waveguide with respect to the fluid interface. The interaction region of the evanescent wave and the fluid is defined by the geometry of the waveguide and can be chosen in order to maximize the signal-to-noise ratio (SNR) of the measurement and/or to optimize the dynamic range. For example, SNR may be increased through spectral filtering (e.g., by using Bragg grating).

This technique also allows for fixed positioning of several waveguides with respect to one another and to the interface. Conversion of the substrate portions to waveguide may be accomplished by "writing" the waveguides into the substrate, such as, for example, by using femtosecond laser pulses from a computer numerically controlled machine tool rig. For femtosecond laser pulsing, a combination of nonlinear absorption through photoionization and avalanche ionization results in the deposition of energy in a small volume around the focus, which may be tightly focused inside a bulk transparent material (i.e., the substrate). The process is given higher order absorption inducing local perturbations in the substrate. In glass, these are defect centers, e.g., given by peroxy radicals and hyperfine structural changes of non-bridging oxygen hole centers. See also Davis, et al., Optics Letters Vol. 21, No. 21 (1996). This pinpoint energy deposition may induce local modification of the refractive index inside the glass network of the substrate by various physical phenomena which are not completely understood. For CNC controlled laser written waveguides, the waveguide geometry, and in particular the length and closeness of the waveguide to the evanescent interaction region at the surface, can be established with a heretofore unknown degree of accuracy and precision.

Method embodiments may include conveying in the borehole an evanescent wave measurement instrument including a substrate and placing the substrate into contact with a downhole fluid such that at least a portion of the substrate is immersed in the downhole fluid. Each of the embodiments herein may be used in a variety of settings in both drilling and non-drilling environments.

Figure 1A:
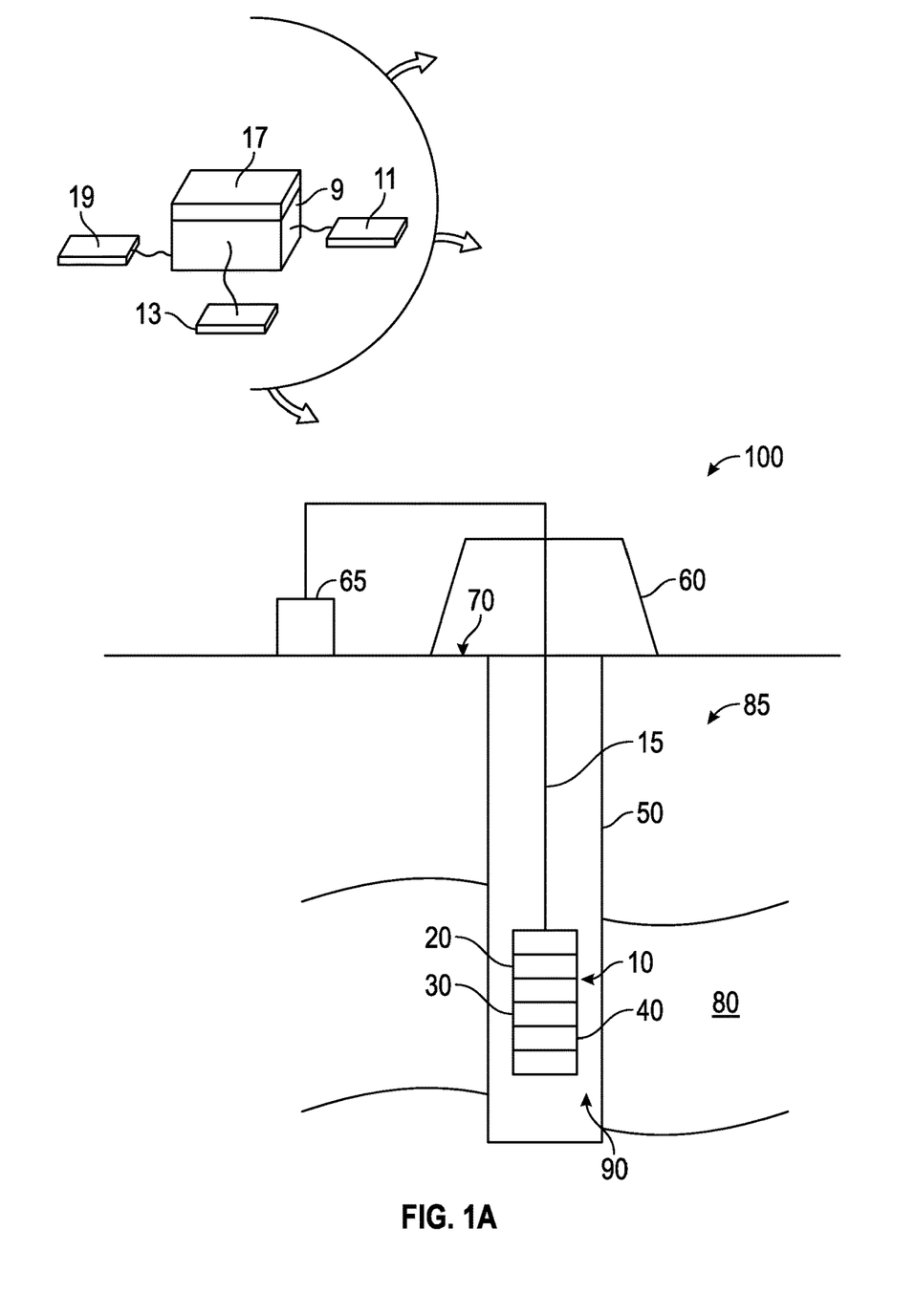
FIG. 1A schematically illustrates a system having a downhole tool configured to acquire information for estimating a downhole parameter of interest using at least one evanescent wave measurement instrument in accordance with embodiments of the present disclosure.

FIG. 1A schematically illustrates a system 100 having a downhole tool 10 configured to acquire information for estimating a downhole parameter of interest (e.g., a value of a property of the formation 80, the borehole 50, or downhole fluid 90 therein) using at least one evanescent wave measurement instrument 40. The at least one evanescent wave measurement instrument 40 is responsive to the parameter of interest. Non-limiting examples of downhole fluids include drilling fluids, return fluids, formation fluids, production fluids containing one or more hydrocarbons, oils and solvents used in conjunction with downhole tools, water, brine, engineered fluids, and combinations thereof.

The system 100 may include a conventional derrick 60 erected on a derrick floor 70. A conveyance device (carrier 15) which may be rigid or non-rigid, may be configured to convey the downhole tool 10 into wellbore 50 in proximity to a volume of interest 80 of an earth formation 85. The carrier 15 may be a drill string, coiled tubing, a slickline, an e-line, a wireline, etc. Downhole tool 10 may be coupled or combined with additional tools e.g., some or all the information processing system (inset). Thus, depending on the configuration, the tool 10 may be used during drilling and/or after the wellbore 50 has been formed. As described herein, "borehole" or "wellbore" refers to a single hole that makes up all or part of a drilled well. While a land system is shown, the teachings of the present disclosure may also be utilized in offshore or subsea applications. The carrier 15 may include embedded conductors for power and/or data for providing signal and/or power communication between the surface and downhole equipment (e.g., a seven conductor cable). The carrier 15 may include a bottom hole assembly, which may include a drilling motor for rotating a drill bit.

Downhole fluid (e.g., drilling fluid, or 'mud') 90 may be present between the formation 85 and the downhole tool 10. A surface control system 65 receives signals from evanescent wave measurement instrument(s) 40 and other sensors used in the system 100 and processes such signals according to programmed instructions provided to the surface control system 65. The surface control system 65 may display desired parameters and other information on a display/monitor that is utilized by an operator. The surface control system 65 may further communicate with a downhole control system 20 at a suitable location on downhole tool 10. The surface control system 65 may process data relating to the operations and data from the sensors 40, and may control one or more downhole operations performed by system 100.

In one embodiment, electronics 30 associated with sensors 40 may be configured to record and/or process the information obtained. Certain embodiments of the present disclosure may be implemented with a hardware environment that includes an information processor 17, an information storage medium 13, an input device 11, processor memory 9, and may include peripheral information storage medium 19. The hardware environment may be in the well, at the rig, or at a remote location. Moreover, the several components of the hardware environment may be distributed among those locations. The input device 11 may be any data reader or user input device, such as data card reader, keyboard, USB port, etc. The information storage medium 13 stores information provided by the detectors. Information storage medium 13 may include any non-transitory computer-readable medium for standard computer information storage, such as a USB drive, memory stick, hard disk, removable RAM, EPROMs, EAROMs, flash memories and optical disks or other commonly used memory storage system known to one of ordinary skill in the art including Internet based storage. Information storage medium 13 stores a program that when executed causes information processor 17 to execute the disclosed method. Information storage medium 13 may also store the formation information provided by the user, or the formation information may be stored in a peripheral information storage medium 19, which may be any standard computer information storage device, such as a USB drive, memory stick, hard disk, removable RAM, or other commonly used memory storage system known to one of ordinary skill in the art including Internet based storage. Information processor 17 may be any form of computer or mathematical processing hardware, including Internet based hardware. When the program is loaded from information storage medium 13 into processor memory 9 (e.g. computer RAM), the program, when executed, causes information processor 17 to retrieve detector information from either information storage medium 13 or peripheral information storage medium 19 and process the information to estimate a parameter of interest. Information processor 17 may be located on the surface or downhole.

The term "information" as used herein includes any form of information (analog, digital, EM, printed, etc.). As used herein, a processor is any information processing device that transmits, receives, manipulates, converts, calculates, modulates, transposes, carries, stores, or otherwise utilizes information. In several non-limiting aspects of the disclosure, an information processing device includes a computer that executes programmed instructions for performing various methods. These instructions may provide for equipment operation, control, data collection and analysis and other functions in addition to the functions described in this disclosure. The processor may execute instructions stored in computer memory accessible to the processor, or may employ logic implemented as field-programmable gate arrays ('FPGAs'), application-specific integrated circuits ('ASICs'), other combinatorial or sequential logic hardware, and so on.

To perform the treatments during a single trip, the tool may use a high bandwidth transmission to transmit the information acquired by detectors 20, 30 to the surface for analysis. For instance, a communication line for transmitting the acquired information may be an optical fiber, a metal conductor, or any other suitable signal conducting medium. It should be appreciated that the use of a "high bandwidth" communication line may allow surface personnel to monitor and control operations in "near real-time."

One point of novelty of the system illustrated in FIG. 1A is that the surface control system 65 and/or the downhole control system 20 are configured to perform certain methods (discussed below) that are not in the prior art. A surface control system or downhole control system may be configured to control the tool described above and any incorporated sensors and to estimate a parameter of interest according to methods described herein.

Figure 1B:
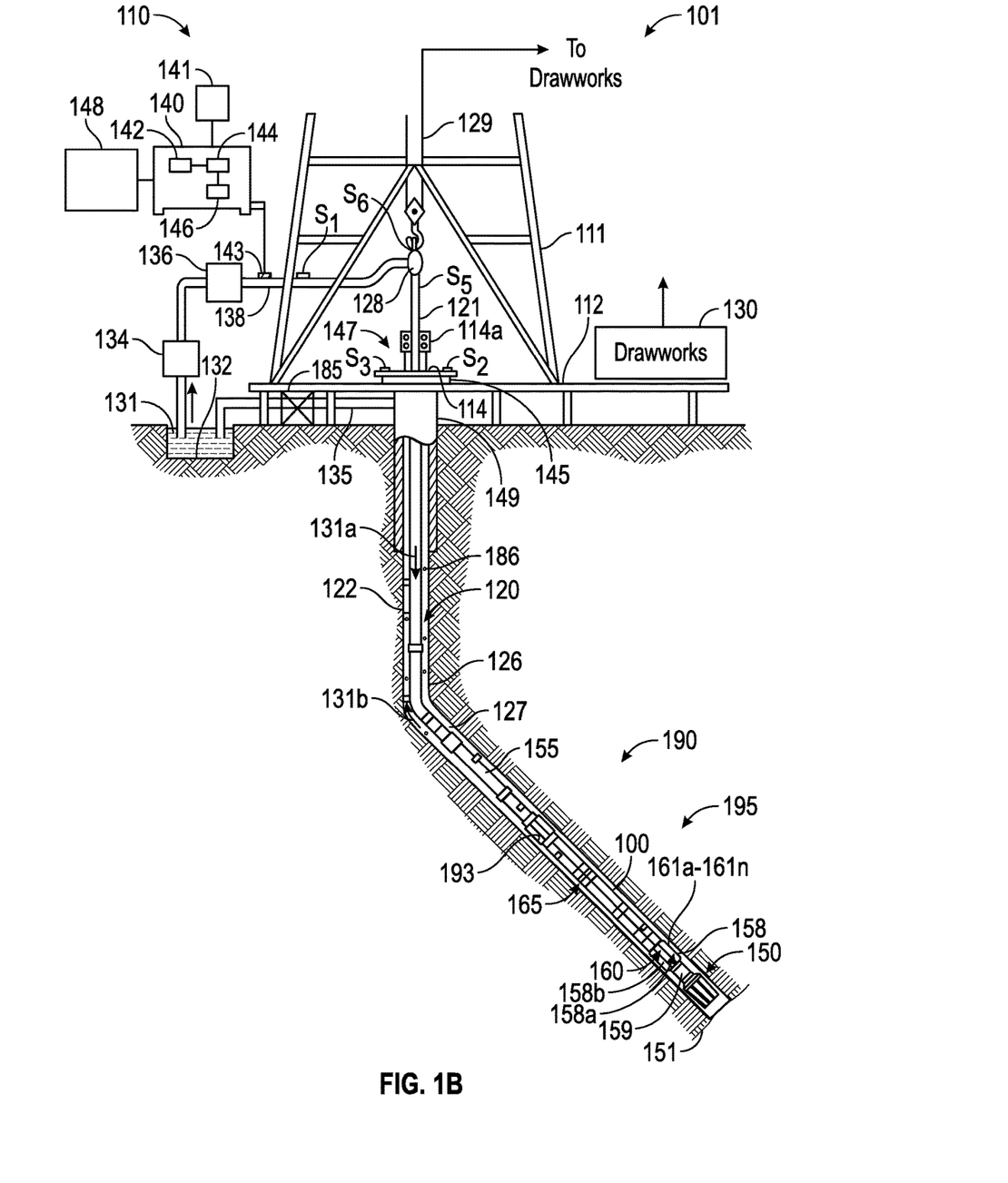
FIG. 1B shows an exemplary embodiment of an MWD system for evaluation of an earth formation using measurements from an evanescent wave measurement tool.

Aspects of the present disclosure are subject to application in various different embodiments. In some general embodiments, carrier 15 is implemented as a tool string of a drilling system, and measurements taken in the borehole may be characterized as "logging-while-drilling" (LWD) or "measurement-while-drilling" (MWD) operations. FIG. 1B shows an exemplary embodiment of an MWD system for evaluation of an earth formation using measurements from an evanescent wave measurement tool. The system 101 includes a carrier 111 that is shown disposed in a wellbore or borehole 126 that penetrates at least one earth formation 195. The system 101 also includes a tool 110 configured for taking evanescent measurements in the borehole.

FIG. 1B shows a drill string 120 including a bottomhole assembly (BHA) 190 conveyed in the borehole 126 as the carrier. The drilling system 101 includes a conventional derrick 111 erected on a platform or floor 112 which supports a rotary table 114 that is rotated by a prime mover, such as an electric motor (not shown), at a desired rotational speed. A tubing (such as jointed drill pipe 122), having the drilling assembly 190, attached at its bottom end extends from the surface to the bottom 151 of the borehole 126. A drill bit 150, attached to drilling assembly 190, disintegrates the geological formations when it is rotated to drill the borehole 126. The drill string 120 is coupled to a drawworks 130 via a Kelly joint 121, swivel 128 and line 129 through a pulley. Drawworks 130 is operated to control the weight on bit ("WOB"). The drill string 120 may be rotated by a top drive (not shown) instead of by the prime mover and the rotary table 114. Alternatively, a coiled-tubing may be used as the tubing 122. A tubing injector 114a may be used to convey the coiled-tubing having the drilling assembly attached to its bottom end. The operations of the drawworks 130 and the tubing injector 114a are known in the art and are thus not described in detail herein.

It should be understood that embodiments of the present disclosure are well suited for use in wells having various configurations including horizontal wells, deviated wells, slanted wells, multilateral wells and so on. Accordingly, use of directional terms herein (e.g., above, below, upper, lower, upward, downward, topmost, lowermost, uphole, downhole, etc) refer to the direction of travel along the borehole either toward or away from the surface, with the upward direction being toward the surface and the downward direction being away from the surface.

A suitable drilling fluid 131 (also referred to as the "mud") from a source 132 thereof, such as a mud pit, is circulated under pressure through the drill string 120 by a mud pump 134. The drilling fluid 131 passes from the mud pump 134 into the drill string 120 via a discharger 136 and the fluid line 138. The drilling fluid 131a from the drilling tubular discharges at the borehole bottom 151 through openings in the drill bit 150. The returning drilling fluid 131b circulates uphole through the annular space 127 between the drill string 120 and the borehole 126 and returns to the mud pit 132 via a return line 135 and drill cutting screen 185 that removes the drill cuttings 186 from the returning drilling fluid 131b. A sensor S1 in line 138 provides information about the fluid flow rate. A surface torque sensor S2 and a sensor S3 associated with the drill string 120 respectively provide information about the torque and the rotational speed of the drill string 120. Tubing injection speed is determined from the sensor S5, while the sensor S6 provides the hook load of the drill string 120.

Well control system 147 is placed at the top end of the borehole 126. The well control system 147 includes a surface blow-out-preventer (BOP) stack 115 and a surface choke 149 in communication with a wellbore annulus 127. The surface choke 149 can control the flow of fluid out of the borehole 126 to provide a back pressure as needed to control the well.

In some applications, the drill bit 150 is rotated by only rotating the drill pipe 122. However, in many other applications, a downhole motor 155 (mud motor) disposed in the BHA 190 also rotates the drill bit 150. The rate of penetration (ROP) for a given BHA largely depends on the WOB or the thrust force on the drill bit 150 and its rotational speed.

A surface control unit or controller 140 receives signals from the downhole sensors and devices via a sensor 143 placed in the fluid line 138 and signals from sensors S1-S6 and other sensors used in the system 101 and processes such signals according to programmed instructions provided to the surface control unit 140. The surface control unit 140 displays drilling parameters and other parameters of interest related to the borehole, formation, and drilling operations, and other information on a display/monitor 141 that is utilized by an operator to control the drilling operations. The surface control unit 140 may be a computer-based unit that may include a processor 142 (such as a microprocessor), a storage device 144, such as a solid-state memory, tape or hard disc, and one or more computer programs 146 in the storage device 144 that are accessible to the processor 142 for executing instructions contained in such programs. The surface control unit 140 may further communicate with a remote control unit 148. The surface control unit 140 may process data relating to the drilling operations, data from the sensors and devices on the surface, and data received from downhole; and may control one or more operations of the downhole and surface devices. The data may be transmitted in analog or digital form.

The BHA 190 may include a tool 110 configured for performing evanescent measurements. The BHA 190 may also contain other formation evaluation sensors or devices (also referred to as measurement-while-drilling ("MWD") or logging-while-drilling ("LWD") sensors) determining resistivity, density, porosity, permeability, acoustic properties, nuclear-magnetic resonance properties, formation pressures, properties or characteristics of the fluids downhole and other desired properties of the formation 195 surrounding the BHA 150. For convenience, all such sensors are generally denoted herein by numeral 165. The BHA 190 may further include a variety of other sensors and devices 159 for determining one or more properties of the BHA 190, such as vibration, bending moment, acceleration, oscillations, whirl, stick-slip, weight-on-bit, fluid flow rate, pressure, temperature, rate of penetration, azimuth, tool face, drill bit rotation, etc.

The BHA 190 may include a steering apparatus or tool 158 for steering the drill bit 50 along a desired drilling path. In one aspect, the steering apparatus may include a steering unit 160, having a number of force application members 161a-161n. The force application members may be mounted directly on the drill string, or they may be at least partially integrated into the drilling motor. In another aspect, the force application members may be mounted on a sleeve, which is rotatable about the center axis of the drill string. The force application members may be activated using electro-mechanical, electro-hydraulic or mud-hydraulic actuators. In yet another embodiment the steering apparatus may include a steering unit 158 having a bent sub and a first steering device 158a to orient the bent sub in the wellbore and the second steering device 158b to maintain the bent sub along a selected drilling direction. The steering unit 158, 160 may include near-bit inclinometers and magnetometers.

The drilling system 101 may include sensors, circuitry and processing software and algorithms for providing information about desired drilling parameters relating to the BHA, drill string, the drill bit and downhole equipment such as a drilling motor, steering unit, thrusters, etc. Many current drilling systems, especially for drilling highly deviated and horizontal wellbores, utilize coiled-tubing for conveying the drilling assembly downhole. In such applications a thruster may be deployed in the drill string 120 to provide the required force on the drill bit.

Exemplary sensors for determining drilling parameters include, but are not limited to drill bit sensors, an RPM sensor, a weight on bit sensor, sensors for measuring mud motor parameters (e.g., mud motor stator temperature, differential pressure across a mud motor, and fluid flow rate through a mud motor), and sensors for measuring acceleration, vibration, whirl, radial displacement, stick-slip, torque, shock, vibration, strain, stress, bending moment, bit bounce, axial thrust, friction, backward rotation, BHA buckling, and radial thrust. Sensors distributed along the drill string can measure physical quantities such as drill string acceleration and strain, internal pressures in the drill string bore, external pressure in the annulus, vibration, temperature, electrical and magnetic field intensities inside the drill string, bore of the drill string, etc. Suitable systems for making dynamic downhole measurements include COPILOT, a downhole measurement system, manufactured by BAKER HUGHES INCORPORATED.

The drilling system 101 can include one or more downhole processors at a suitable location such as 193 on the BHA 190. The processor(s) can be a microprocessor that uses a computer program implemented on a suitable non-transitory computer-readable medium that enables the processor to perform the control of system 101 and processing of information, such as information from the sensors. The non-transitory computer-readable medium may include one or more ROMs, EPROMs, EAROMs, EEPROMs, flash memories, RAMs, hard drives and/or optical disks. Other equipment such as power and data buses, power supplies, and the like will be apparent to one skilled in the art. In one embodiment, the MWD system utilizes mud pulse telemetry to communicate data from a downhole location to the surface while drilling operations take place. The surface processor 142 can process the surface measured data, along with the data transmitted from the downhole processor, to evaluate the formation.

Surface processor 142 or downhole processor 193 may also be configured to control steering apparatus 158, mud pump 134, drawworks 130, rotary table 114, downhole motor 155, other components of the BHA 190, or other components of the drilling system 101. Surface processor 142 or downhole processor 193 may be configured to control sensors described above and to estimate a parameter of interest according to methods described herein.

Control of these components may be carried out using one or more models using methods described below. For example, surface processor 142 or downhole processor 193 may be configured to modify drilling operations i) autonomously upon triggering conditions, ii) in response to operator commands, or iii) combinations of these. Such modifications may include changing drilling parameters, steering the drillbit (e.g., geosteering), altering the drilling fluid program, activating well control measures, and so on. Control of these devices, and of the various processes of the drilling system generally, may be carried out in a completely automated fashion or through interaction with personnel via notifications, graphical representations, user interfaces and the like. Reference information accessible to the processor may also be used. In some general embodiments, surface processor 142, downhole processor 193, or other processors (e.g. remote processors) may be configured to operate the evanescent tool 110 to generate an evanescent wave and measure signals.

The system 101 may include any number of downhole tools for various processes including formation drilling, geosteering, and formation evaluation (FE) for making electrical measurements versus depth and/or time of one or more physical properties in or around a borehole, including a volume of interest of the formation intersected by the borehole. The tool 110 may be included in or embodied as a BHA, drillstring component or other suitable carrier.

While a drill string 120 is shown as a conveyance device for tool 110, it should be understood that embodiments of the present disclosure may be used in connection with tools conveyed via rigid (e.g. jointed tubular or coiled tubing) as well as non-rigid (e. g. wireline, slickline, e-line, etc.) conveyance systems. The drilling system 101 may include a bottomhole assembly and/or sensors and equipment for implementation of embodiments of the present disclosure on either a drill string or a wireline.

Mathematical models, look-up tables, or other models representing relationships between the signals and the parameter values may be used to characterize the borehole, downhole fluid, operations in the formation or the formation itself, optimize one or more operational parameters of a production or development, and so on. The system may carry out these actions through notifications, advice, and/or intelligent control. Various types of downhole parameters may be determined using measurements in accordance with the present disclosure and making evaluations in accordance with embodiments disclosed herein.

Figure 2:
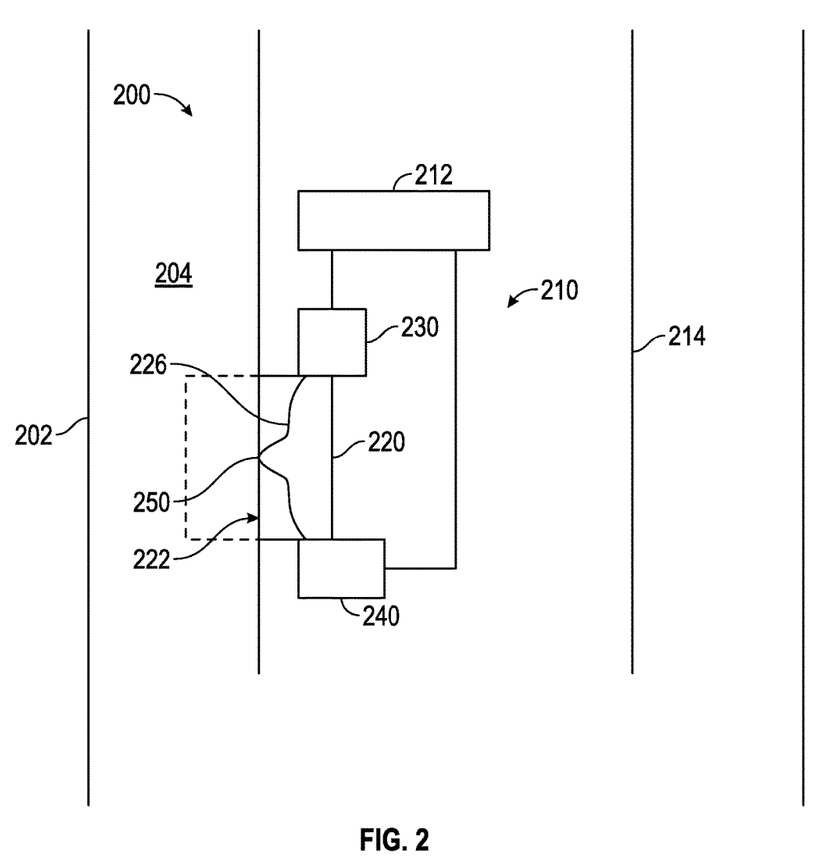
FIG. 2 illustrates a tool including at least one evanescent wave measurement instrument in accordance with embodiments of the invention.

FIG. 2 illustrates a tool including at least one evanescent wave measurement instrument in accordance with embodiments of the invention. Referring to FIG. 2, tool 200 includes at least one evanescent wave measurement instrument and is configured to be conveyed in a borehole 202. An evanescent wave measurement instrument 210 configured to measure a downhole parameter is mounted on the tool 200. In some embodiments, some (or all) of evanescent wave measurement instrument 210 may protrude from the tool body 212 into the borehole 202. In other embodiments, the tool 200 may include a fluid testing assembly configured to extract downhole fluid from the borehole and deliver the fluid to the evanescent wave measurement instrument 210 for testing. The fluid testing assembly may include a sample chamber which may be filled and emptied via the use of various valves, or may operate using a continuous flow line.

The instrument 210 comprises a bulk substrate 220 having a portion (e.g., face 222) immersed in the downhole fluid 204, forming an interface 250 between the substrate 220 and the fluid 204. The substrate may include silica-based glasses (e.g., fused silica), fluoride glasses based on ZrF4 (e.g., ZrF4-BaF2-LaF3-AlF3-NaF ('ZBLAN')), chalcogenide glasses, polymers, and so on. For substrate protection, a diamond-like carbon (DLC) layer may be employed on the substrate, which can be tuned in electrical and optical properties along with applying the appropriate deposition mechanism. Gallium lanthanum sulphide may be used for realizing waveguides in a wide range of near-infrared (NIR) and mid-infrared (mid-IR) spectra.

A waveguide 226 is formed in an interior of the substrate 220. The structures of the waveguide may be written using femtosecond laser pulsing. An electromagnetic energy source 230 provides energy to the waveguide 226 for the evanescent wave. As one example, a light emitting diode is optically coupled to the waveguide 226 to provide an infrared light beam. A detector (e.g., a photodetector) 240 optically coupled to the waveguide detects electromagnetic signals (e.g., light) received from the waveguide. Tool 200 may include circuitry for making measurements using the evanescent wave measurement instrument 210. Circuitry may include control unit 212 operatively connected to source 230 and detector 240. Controller 212 may be implemented as the at least one processor described above with reference to FIG. 1A & 1B or may be an additional processor or other supporting circuitry. Controller 212 may be located at the instrument, at other locations in the tool (including, for example, in other subs), or at the surface.

In operation, the instrument may be controlled by control unit 212 (e.g., a processor), which actuates the energy source 230 while the portion is immersed in the downhole fluid and operates and receives measurement information (e.g., data) from detector 240. propagating in a segment of the waveguide responsive to an application of electromagnetic energy to the waveguide The waveguide 226 is configured to optimize the light guided inside the waveguide only. Light propagation inside the waveguide results in an evanescent wave protruding into the substrate. A segment of the substrate 250 is located close enough to the substrate surface such that the evanescent wave protrudes not only into the substrate, but also into the fluid 204. The evanescent wave and with this the electromagnetic wave inside of the waveguide is attenuated through absorption in the fluid.

An evanescent (harmonic) wave is formed where the waveguide is proximate the interface 250, resulting in an interaction between the evanescent wave and the downhole fluid. The evanescent wave penetrates into the fluid 204 to a penetration depth, dp, and is approximated by:

$$E = E_0 e^{(-z/dp)}$$

where z represents a distance normal to the interface between the waveguide and the fluid and $E_0$ represents an amplitude of a wave at z=0. A penetration depth, d, into the fluid is given by:

$$dp = \lambda (2\pi n_1)(\sin^2\theta - (n_1/n_2)^2)^{0.5}$$

where $\lambda$ represents a wavelength of light, $n_1$ represents a refractive index (RI) of the waveguide, and $n_2$ represents the refractive index of the fluid.

Figure 3A:
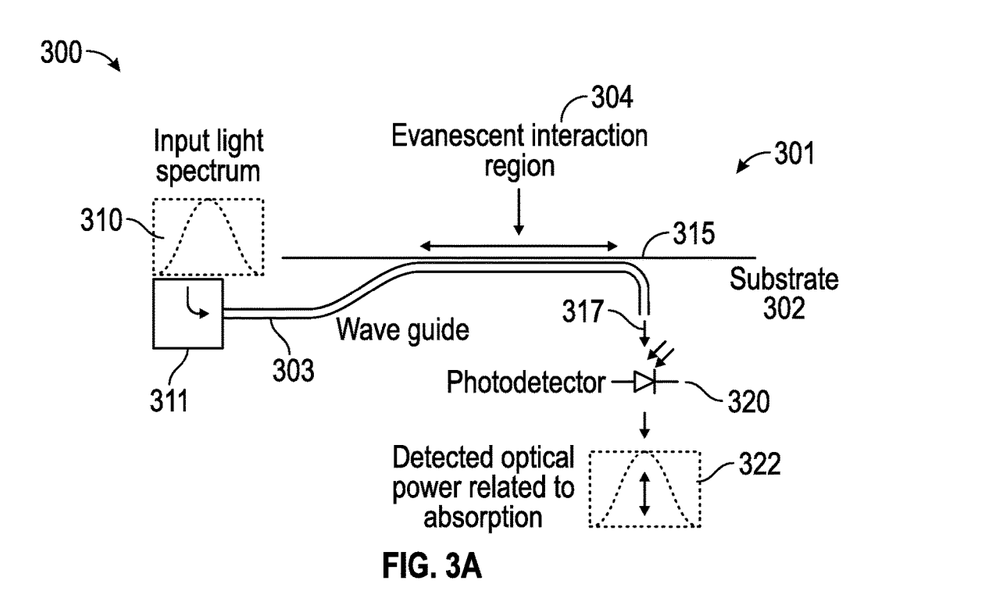
FIGS. 3A &3B illustrate evanescent wave measurement instruments in accordance with embodiments of the present disclosure.
Figure 3B:
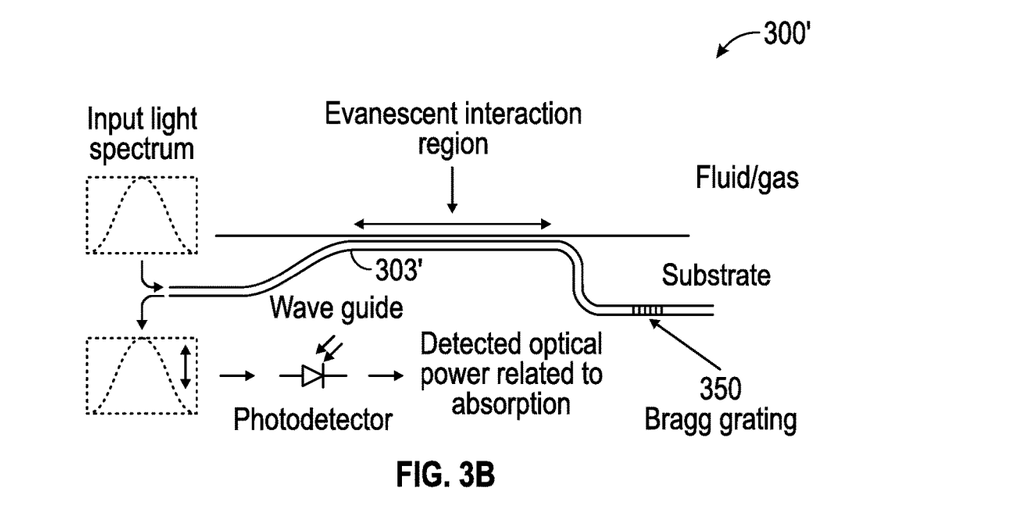

FIGS. 3A & 3B illustrate evanescent wave measurement instruments in accordance with embodiments of the present disclosure. The evanescent wave measurement instrument 300 includes a bulk substrate 302 configured in contact with a downhole fluid 301 such that a portion of the substrate is immersed in the downhole fluid. A waveguide 303 is formed in an interior of the substrate. The waveguide 303 is geometrically configured (via dimensions and path within the substrate) to generate an interaction between the downhole fluid and an evanescent wave propagating in a segment of the waveguide in an interaction region. The waveguide generates the reaction responsive to an application of electromagnetic energy to the waveguide while the portion is immersed in the downhole fluid. Here, the application of electromagnetic energy is implemented as light 310 is input to the waveguide 303 via optical coupling 311. The waveguide 303 is configured to produce the interaction via its path, which extends to a region proximate the interface 315, in which it extends parallel to and close to the interface, as well as via the refractive index of the waveguide. Photodetector 320 generates measurement information 322 indicative of the downhole fluid in response to electromagnetic signals 317 received from the waveguide 303 responsive to partial absorption of the electromagnetic energy resulting from the interaction. That is, the evanescent field attenuation from light traveling close to the substrate is estimated using the signals received from the photodetector 320.

Referring to FIG. 3B, instrument 300' is configured identically to instrument 300, with the exception that waveguide 303' includes Bragg grating 350 written into the waveguide using, for example, femtosecond laser pulses in addition to the waveguide. Bragg grating 350 only reflects a desired portion of the light traveling in the waveguide. The reflection spectrum of the Bragg grating may be configured to match the spectral feature desired to be detected (e.g. wavelength). That is, the Bragg grating inside the waveguide may be configured such that only a distinct spectroscopic feature is reflected. For example, the portion of reflected light may be configured to match an absorption line of the fluid, which allows using a simple photodetector instead of a spectrometer in order to detect the absorption correlated with a desired spectral feature (e.g., a gas absorption line). For example, absorption of light in wavelengths characteristic of particular fluids may be detected, such as, for example, methane, ethane, propane, butane, hydrogen sulfide, carbon dioxide, and so on. This substitution greatly reduces complexity and cost. Alternatively, a single feature can be detected in transmission of a waveguide close to the surface, if a Bragg grating or mismatched waveguide Bragg grating coupler is used to filter the light in front of the photodetector. In various embodiments, the distal end of the waveguide may include a mirror or other mechanism used to reflect the light in the waveguide.

The waveguide path may be asymmetric with respect to the substrate. The substrate may be a bulk substrate, e.g., more than 1 millimeter in three dimensions. The bulk substrate may have a minimum thickness of at least 100 μm in a direction perpendicular to the interface. The ratio of the minimum thickness of the substrate to the maximum thickness of the waveguide may be at least 5 to 1, and may be more than 10 to 1. At a closest point of the segment to the interface, a distance from the segment to the interface may be substantially zero.

Figure 4:
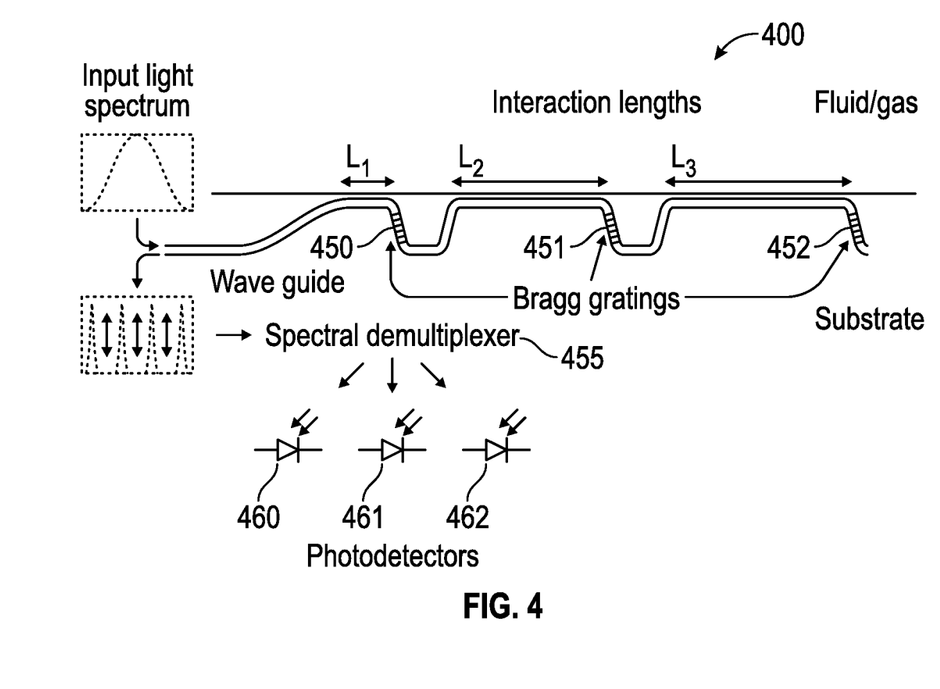
FIG. 4 illustrates another evanescent wave measurement instrument in accordance with embodiments of the present disclosure.

FIG. 4 illustrates another evanescent wave measurement instrument in accordance with embodiments of the present disclosure. Instrument 400 uses multiple Bragg gratings 450, 451, 452, so that the absorption of several of features can be detected. A spectral demultiplexer 455, such as a set of additional Bragg gratings on the detector side, separates the signals to a corresponding set of photodetectors 460, 461, 462, with one Bragg grating and one photodetector for each spectroscopic feature. An application would be the detection of gas concentrations in drilling fluids. This could also be used as part of a kick detection solution by using waveguide segments corresponding to various concentrations of gas within the fluid and generating an alert notification when concentrations over a threshold are detected. The light interacts with the fluid on different waveguide segments (L1, L2, L3, etc.) having various different lengths, which provides a dramatic increase in the system dynamics. That is, the light may be strongly modulated by small changes in concentration, resulting in lowered sensitivity outside of a specific range. By employing segments of varying lengths, longer waveguide sections (e.g., L3) facilitate detection of weak concentrations of the fluid, whereas smaller waveguide sections allow detection of stronger concentrations. The dynamic range is increased as the attenuation scales directly with the waveguide-to-fluid interaction length. Bragg wavelengths of the serial or parallel gratings may be selected to coincide with the selected spectral feature, but slightly offset one to another to facilitate spectral discrimination of the different length of interaction. High concentration, and thus strong attenuation, for example, may result in a null signal from L3 and L2, but L1 might still see some reflectance as the interaction length is short. In contrast, for weak concentrations (attenuations) L1 and L2 may be substantially unattenuated, so L3 sees attenuation as the interaction is long.

Figure 5:
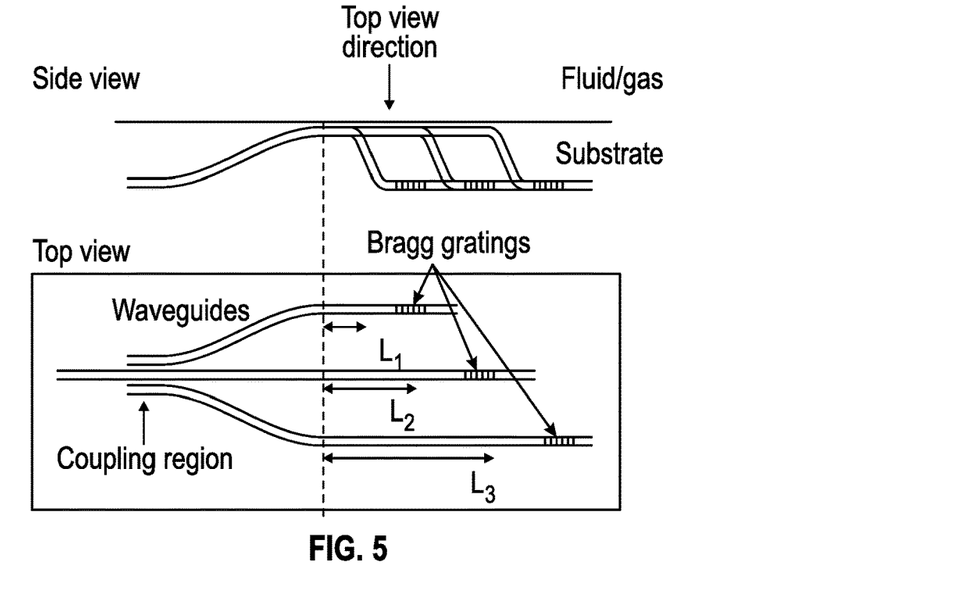
FIG. 5 illustrates another evanescent wave measurement instrument in accordance with embodiments of the present disclosure having waveguides operating in parallel.

FIG. 5 illustrates another evanescent wave measurement instrument in accordance with embodiments of the present disclosure having waveguides operating in parallel. The dynamic range extension as described above with respect to FIG. 4 could also be implemented by distributing several waveguides, each with a corresponding waveguide having different lengths L1, L2, L3, over the substrate-to-liquid interface. The waveguides can be fed by a single light source and connected via evanescent couplers.

Figure 6:
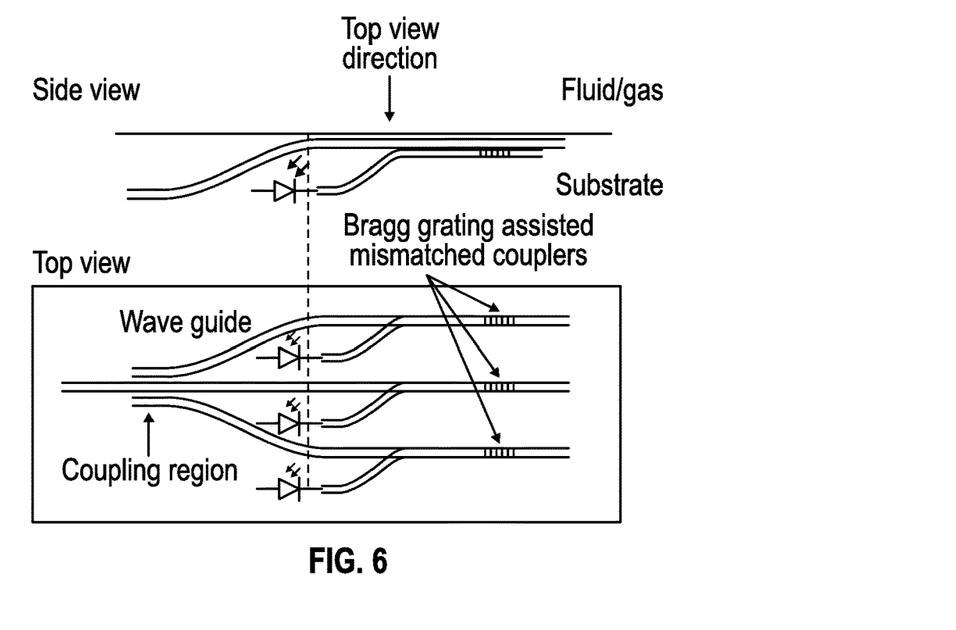
FIG. 6 illustrates another evanescent wave measurement instrument in accordance with embodiments of the present disclosure.

FIG. 6 illustrates another evanescent wave measurement instrument in accordance with embodiments of the present disclosure. By setting the lengths of waveguide equal, it is possible to realize a position-sensitive measurement, e.g. for detecting parameter gradients (e.g., concentration gradients). Before or after the evanescent interaction with the fluid, a mismatched Bragg grating assisted coupler may be used to couple a specific spectral part of the light (e.g., the same spectrum for all waveguides), and the transmitted light power is detected by a single photodetector for each waveguide. Relying on the capacity of writing three dimensional shapes of waveguides, it can be assured with a high degree of accuracy that the length of the waveguides is identical (not only in the interrogation region, but also in total), such that propagation losses impact each channel in the same way. Thus, using several waveguides of identical interaction length and mismatched Bragg-grating assisted couplers (with Bragg grating written either in the sensing or in the detector waveguides in the coupler region), improved gas detection can be realized.

In other implementations, two sets of waveguides can be used where the substrate includes a plurality of waveguides formed in an interior of the substrate. A first set of waveguides may be exposed to a reference sample, while the remaining waveguide of the other set are configured as above to interact with the fluid. The reference waveguide of the plurality of waveguides is thus geometrically configured to generate a respective interaction between a reference fluid and a corresponding evanescent wave propagating in a corresponding segment of the reference waveguide. A detector is configured to generate measurement information indicative of the reference fluid in response to electromagnetic signals received from the reference waveguide. The reference sample may be used to increase absolute sensitivity or for compensating pressure- or temperature related spectroscopic shifts of the downhole fluid. A processor configured to estimate the parameter of interest using measurement information generated from the reference waveguide.

In other general embodiments, a multi-waveguide spectrometer is realized by choosing the central wavelengths of adjacent Bragg-grating-assisted couplers to be slightly shifted with respect to one another, which results in absorption signals for adjacent spectral intervals. In this way a spectroscopic measurement may be achieved while reducing complexity of the employed detector, such as, for example, a simple photodetector.

Some embodiments may employ Bragg grating structures written close to the interface, such that strong evanescent coupling takes place in the Bragg reflection region. This couple may induce, depending on the refractive index of the fluid, a shift in the effective refractive index of the waveguide and, thus, of the Bragg wavelength. This can be detected using an interrogator system detecting the central wavelength shift of the reflected spectrum.

In operation, electromagnetic energy may be applied to one or more waveguides in a substrate to generate an interaction between the downhole fluid and an evanescent wave propagating in a segment of waveguide formed in the substrate. The interaction may result in partial absorption of the electromagnetic energy by the downhole fluid, as a result of the wave extending into an interaction region within the downhole fluid. The evanescent wave phenomenon, as employed herein for measurement, occurs due to the introduction of electromagnetic energy to a waveguide which is properly configured via its physical layout within the substrate. Methods may further include generating measurement information by detecting electromagnetic signals from the waveguide responsive to the partial absorption of the electromagnetic energy resulting from the interaction; and estimating a parameter of interest using the measurements.

Figure 7:
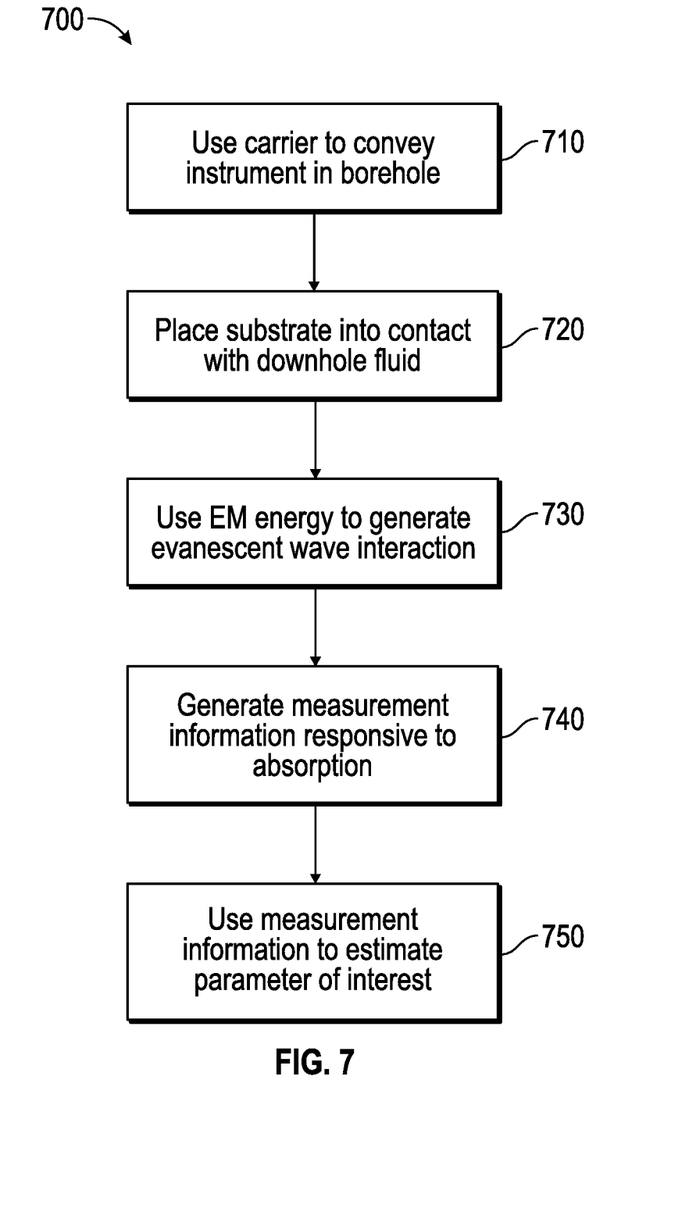
FIG. 7 shows a flow chart for estimating at least one downhole parameter in accordance with embodiments of the present disclosure.

FIG. 7 shows a flow chart 700 for estimating at least one downhole parameter according to one embodiment of the present disclosure. In optional step 710, an evanescent wave measurement instrument responsive to a downhole parameter is conveyed in the borehole using a carrier. The evanescent wave measurement instrument includes a substrate. In the borehole, a downhole measurement is made. Step 720 includes placing the substrate into contact with a downhole fluid such that at least a portion of the substrate is immersed in the downhole fluid. Step 730 comprises using electromagnetic energy to generate an interaction between the downhole fluid and an evanescent wave propagating in a segment of waveguide formed in the substrate. The evanescent wave extends into an interaction region within the downhole fluid. The interaction results in partial absorption of the electromagnetic energy by the downhole fluid.

Step 740 comprises generating measurement information by detecting electromagnetic signals from the waveguide responsive to the partial absorption of the electromagnetic energy resulting from the interaction. Step 750 comprises estimating a parameter of interest using the measurement information.

Herein, "information" may include raw data, processed data, analog signals, and digital signals. Estimation of the parameter may include the use of a model. In some embodiments, the model may include, but is not limited to, one or more of: (i) a mathematical equation, (ii) an algorithm, (iii) an deconvolution technique, and so on. The at least one parameter of interest may include, but is not limited to, one or more of: (i) viscosity, (ii) gas concentration, (iii) gas concentration gradient.

In some aspects, this disclosure relates to estimating a parameter of interest related to a borehole fluid of a borehole in an earth formation. The parameter of interest may be a physical characteristic of the fluid, such as, for example, density.

During establishment or servicing of a hydrocarbon producing well, undesirable conditions may occur which may be hazardous to equipment and personnel. For example, during drilling, high pressure formation fluid can invade the wellbore and displace drilling fluid from the well. This undesirable condition is known in the industry as a "kick." The resulting pressure interaction in the wellbore may lead to an uncontrolled flow of fluids from a well, known as a "blow-out." Thus, conventionally, the mud weight of a drilling fluid circulated in the well during drilling may be selected to provide an appropriate hydrostatic pressure that minimizes the risk and impact of a "kick." During drilling, the pressure of the drilling mud may be maintained within a pressure window by a mud program using pore pressure information. Accurately determining the pressure window enables efficient drilling of the borehole while preventing damage.

Additionally, well control devices (e.g., surface blowout prevention systems or hydraulic isolation devices) may be used to protect against blowouts. When a kick is detected, a well control device may be activated to "shut-in" a well to seal off and/or exert control over the kick. This may be followed by circulating heavy mud through the choke to balance the kick pressure before the well control device is disengaged.

This process is expensive and time consuming, and interrupts more beneficial activities in the wellbore. Avoiding the unnecessary activation of a well control device (or system of well-control devices) is therefore desirable. Activating a well control device when required to prevent a blowout is also desirable. Thus, accurately determining the presence or absence of a kick is beneficial to enable efficient drilling of the borehole while preventing damage.

The term "conveyance device" as used above means any device, device component, combination of devices, media and/or member that may be used to convey, house, support or otherwise facilitate the use of another device, device component, combination of devices, media and/or member. Exemplary non-limiting conveyance devices include drill strings of the coiled tube type, of the jointed pipe type and any combination or portion thereof. Other conveyance device examples include casing pipes, wirelines, wire line sondes, slickline sondes, drop shots, downhole subs, BHA's, drill string inserts, modules, internal housings and substrate portions thereof, self-propelled tractors. As used above, the term "sub" refers to any structure that is configured to partially enclose, completely enclose, house, or support a device. By "uncooled" it is meant without active cooling using the electrocaloric effect, as contrasted with insulation or other passive temperature control measures. The term "information" as used above includes any form of information (Analog, digital, EM, printed, etc.).

The term "information processing device" herein includes, but is not limited to, any device that transmits, receives, manipulates, converts, calculates, modulates, transposes, carries, stores or otherwise utilizes information. An information processing device may include a microprocessor, resident memory, and peripherals for executing programmed instructions. "Simple photodetector", as used herein, refers to a narrow-band detector having a bandwidth on the order of a single channel of a spectrometer. As used herein, the term "fluid" and "fluids" refers to one or more gasses, one or more liquids, and mixtures thereof. A "downhole fluid" as used herein includes any gas, liquid, flowable solid and other materials having a fluid property, and relating to hydrocarbon recovery. A downhole fluid may be natural or man-made and may be transported downhole or may be recovered from a downhole location. Non-limiting examples of downhole fluids include drilling fluids, return fluids, formation fluids, production fluids containing one or more hydrocarbons, oils and solvents used in conjunction with downhole tools, water, brine, and combinations thereof.

Substantially zero, when used herein in reference to distance, refers to distances sufficient for increased performance in accordance with the techniques disclosed herein, such as, for example, less than 100 µm, less than 50 µm, less than 20 µm, less than 10 µm, less than 5 µm, less than 2 µm, less than 1 µm, down to and include zero distance. Substantially zero, when used herein in reference to signal strength, refers to signal strength of, for example, more than 90 percent attenuated, more than 95 percent attenuated, more than 98 percent attenuated, more than 99 percent attenuated, more than 99.5 percent attenuated, more than 99.9 percent attenuated, up to and including 100 percent signal attenuation (zero signal). Substantially unattenuated, when used herein in reference to signal strength, refers to signal strength, for example, of more than 90 percent, more than 95 percent, more than 98 percent, more than 99 percent, up to and include 100 percent signal.

While the foregoing disclosure is directed primarily to the transversal single-mode behavior of the light propagating along the waveguides, embodiments configured for multi-mode operation would be advantageous in connection with some applications and may also be implemented by one of skill in the art with the aid of the present disclosure by applying customary configuration. These and other various modifications will be apparent to those skilled in the art. It is intended that all variations be embraced by the foregoing disclosure.

What is claimed is:

1. An apparatus for estimating a parameter of interest of a downhole fluid in a borehole intersecting an earth formation, the apparatus comprising:
   an evanescent wave measurement instrument configured for conveyance in a borehole intersecting an earth formation, the borehole filled with a downhole fluid, the evanescent wave measurement instrument comprising:
     a substrate configured for contact with the downhole fluid such that at least a portion of the substrate is immersed in the downhole fluid;
     a waveguide formed in an interior of the substrate, the waveguide comprising a local modification of a refractive index of the substrate, and having a configuration geometrically configured to generate an interaction between the downhole fluid and an evanescent wave arising from electromagnetic energy propagating in a segment of the waveguide responsive to application of electromagnetic energy to the waveguide;

a detector configured to generate measurement information indicative of the downhole fluid in response to electromagnetic signals received from the waveguide, the electromagnetic signals produced responsive to the interaction.

2. The apparatus of claim 1 wherein the interaction results in absorption of at least a portion of the electromagnetic energy propagating in the waveguide.

3. The apparatus of claim 1 wherein the interaction results in a modification of an effective refractive index of the waveguide.

4. The apparatus of claim 1 wherein the configuration includes waveguide dimensions and a waveguide path within the substrate.

5. The apparatus of claim 1 wherein the waveguide path is asymmetric with respect to the substrate.

6. The apparatus of claim 1 wherein the substrate comprises at least one flat surface.

7. The apparatus of claim 1 wherein the substrate comprises a bulk substrate.

8. The apparatus of claim 7 wherein the bulk substrate has a minimum thickness of at least 1 millimeter in a direction perpendicular to the interface.

9. The apparatus of claim 8 wherein the waveguide has a maximum thickness less than 100 µm in a direction perpendicular to a longitudinal axis of the waveguide.

10. The apparatus of claim 1 wherein the ratio of the minimum thickness of the substrate to the maximum thickness of the waveguide is at least 5 to 1.

11. The apparatus of claim 1 wherein waveguide comprises Bragg grating configured to produce a reflection spectrum matching a spectral property detected by the detector.

12. The apparatus of claim 1 wherein waveguide comprises Bragg grating configured to produce a reflection spectrum matching a spectral property double that of a spectral property detected by the detector.

13. The apparatus of claim 1 wherein the waveguide is geometrically configured via dimensions and path within the substrate to generate a second interaction between the downhole fluid and a second evanescent wave arising from electromagnetic energy propagating in a second segment of the waveguide.

14. The apparatus of claim 13 an additional detector configured to generate measurement information indicative of the second interaction.

15. The apparatus of claim 13 wherein the segment has a first length and the second segment has a second length different than the first length.

16. The apparatus of claim 1 wherein:
the substrate includes a plurality of waveguides formed in an interior of the substrate, each waveguide of the plurality of waveguides having a configuration geometrically configured to generate a respective interaction between the downhole fluid and a corresponding evanescent wave arising from electromagnetic energy propagating in a corresponding segment of the respective waveguide; and
at least one detector configured to generate measurement information indicative of each respective interaction.

17. The apparatus of claim 16 wherein the waveguide of the plurality of waveguides has a configuration including first waveguide dimensions and a first waveguide path within the substrate; and a second waveguide of the plurality of waveguides has second waveguide dimensions and a second waveguide path within the substrate, and wherein at least one of: i) the first waveguide dimensions are different than the second waveguide dimensions; and ii) the first waveguide path is different than the second waveguide path.

18. The apparatus of claim 16 wherein the measurement instrument comprises at least one processor configured to measure values of the parameter of interest at a plurality of positions over the substrate and map the values according to position.

19. The apparatus of claim 1 wherein:
the substrate includes a plurality of waveguides formed in an interior of the substrate, with a reference waveguide of the plurality of waveguides geometrically configured via dimensions and path within the substrate to generate a respective interaction between a reference fluid and a corresponding evanescent wave arising from electromagnetic energy propagating in a corresponding segment of the reference waveguide; and
at least one detector configured to generate measurement information indicative of the reference fluid in response to electromagnetic signals received from the reference waveguide;
at least one processor configured to estimate the parameter of interest using measurement information generated from the reference waveguide.

20. The apparatus of claim 1 wherein the waveguide is formed by applying laser pulses to the substrate.

21. The apparatus of claim 1 comprising a processor configured to estimate the parameter of interest using the measurement information.

22. The apparatus of claim 1 wherein the parameter of interest comprises a concentration of a gas in the fluid.

23. The apparatus of claim 22 the processor is configured to use the concentration of the gas to identify an impending kick.

24. The apparatus of claim 1 comprising a carrier associated with the evanescent wave measurement instrument and configured for conveyance in the borehole.

25. A method for estimating a parameter of interest related to well logging in a borehole intersecting an earth formation, the method comprising:
conveying an evanescent wave measurement instrument in the borehole, the evanescent wave measurement instrument comprising a substrate;
placing the substrate into contact with a downhole fluid in the borehole such that at least a portion of the substrate is immersed in the downhole fluid;
using electromagnetic energy to generate an interaction between the downhole fluid and an evanescent wave arising from electromagnetic energy propagating in a segment of waveguide formed in the substrate, the waveguide comprising a local modification of a refractive index of the substrate, the evanescent wave extending into an interaction region within the downhole fluid;
generating measurement information by detecting electromagnetic signals from the waveguide responsive to the interaction;
estimating a parameter of interest using the measurement information; and
rendering the parameter of interest on a display.

* * * * *